United States Patent [19]

Yamaguchi et al.

[11] Patent Number: 5,041,560
[45] Date of Patent: Aug. 20, 1991

[54] FLUORAN COMPOUND

[75] Inventors: Masahiko Yamaguchi, Matsudo; Katsumasa Kikkawa, Tokyo; Michihiro Gonda, Kitamoto, all of Japan

[73] Assignee: Hodogaya Chemical Co., Ltd., Tokyo, Japan

[21] Appl. No.: 377,412

[22] Filed: Jul. 10, 1989

[30] Foreign Application Priority Data

Aug. 24, 1988 [JP] Japan .............................. 63-208164

[51] Int. Cl.[5] .......................................... C07D 493/10
[52] U.S. Cl. .................................................... 549/225
[58] Field of Search ......................................... 549/225

[56] References Cited

U.S. PATENT DOCUMENTS

| | | | |
|---|---|---|---|
| 2,505,470 | 4/1950 | Green | 117/36 |
| 2,505,471 | 4/1950 | Green | 117/36 |
| 2,505,489 | 4/1950 | Green | 117/36 |
| 2,548,366 | 4/1951 | Green et al. | 282/28 |
| 2,723,507 | 7/1955 | Green | 117/36 |
| 2,730,456 | 1/1956 | Green et al. | 117/36 |
| 2,730,457 | 1/1956 | Green et al. | 117/36 |
| 3,418,250 | 12/1968 | Vassiliades | 257/316 |
| 3,442,908 | 5/1969 | Orita et al. | 549/225 |
| 4,151,748 | 5/1979 | Baum | 503/202 |
| 4,687,862 | 8/1987 | Obitsu et al. | 549/224 |

FOREIGN PATENT DOCUMENTS 45-4701 2/1970 Japan .

Primary Examiner—Richard L. Raymond
Attorney, Agent, or Firm—Wenderoth, Lind & Ponack

[57] ABSTRACT

A novel fluoran compound represented by the formula (I):

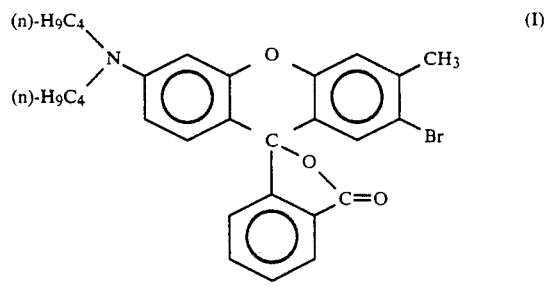

is disclosed.

By using the novel fluoran compound (I) as a chromogenic substance, a pressure-sensitive record material is provided which can develop an image of a clear vermilion color when it contacts a developer of an acidic substance.

1 Claim, No Drawings

FLUORAN COMPOUND

FIELD OF THE INVENTION

The present invention relates to a novel fluoran compound and a record material prepared by using this fluoran compound. More particularly, it relates to a novel fluoran compound as a chromogenic substance which develops a clear vermilion color and to a pressure-sensitive record material having a chromogenic layer containing this fluoran compound.

BACKGROUND OF THE INVENTION

Heretofore, there has been generally known a pressuresensitive copying paper utilizing a color developing reaction between a substantially colorless chromogenic substance and an adsorptive or reactive compound (hereinafter referred to as a developer) which develops a color when it contacts the chromogenic substance. See, for example, U.S. Pat. Nos. 2,505,470; 2,505,471; 2,505,489; 2,548,366; 2,712,507; 2,730,456; 2,730,457 and 3,418,250. Examples of the chromogenic substances are Malachite Green Lactone, Benzoyl Leuco Methylene Blue, Crystal Violet Lactone, Rhodamine B Lactam, 2-(substituted amino)-6-(substituted amino) fluoran, 3-methyl-2,2-spiro- (benzo[f]chromene) and a mixture thereof. Examples of the developers are clay minerals such as acid clay, activated clay, attapulgite, zeolite, bentonite and kaolin; organic acids such as succinic acid, tannic acid, gallic acid and phenolic compounds; and acidic polymers such as a phenol- formaldehyde resin. The chromogenic substance and the developer employed herein are defined as follows from the viewpoint of electronic theory: the chromogenic substance means a substance which develops a color by donating electrons or by accepting protons, and the developer means a substance which accepts electrons or donates protons.

The requirements for the chromogenic substance used in the record material are that it has a high speed of color development, that it has a high color density, that the color-developed chromogenic substance has a desired hue, that it has no sublimability and that the light fastness and heat resistance of the color-developed chromogenic substance are excellent. However, though Crystal Violet Lactone is known as the chromogenic substance developing a blue color, the developed color has poor light fastness. It has thus been desired to develop a chromogenic substance which can satisfy the above-described requirements.

On the other hand, 2-chloro-3-methyl-6-diethylaminofluoran represented by the following formula (A) (hereinafter referred to as compound A) is used as a chromogenic substance which develops a vermilion color though it is inferior in sublimation resistance. See Japanese Examined Patent Publication No. 4701/1970.

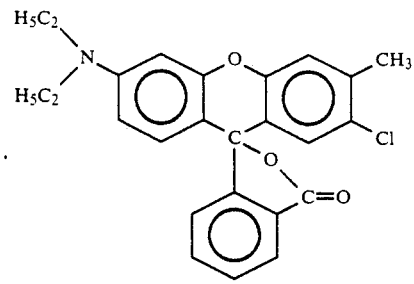

SUMMARY OF THE INVENTION

An object of the present invention is to provide a novel fluoran compound which can solve the above-described prior art problems and which can develop a clear vermilion color having a high speed of color development, a high color density, an excellent light fastness and a good sublimation resistance when the fluoran is utilized as a chromogenic substance.

Further object of the present invention is to provide a novel and improved pressure-sensitive record material using the above-described novel fluoran compound as a chromogenic substance.

According to one aspect of the present invention, there is provided a novel fluoran compound represented by the following formula (I):

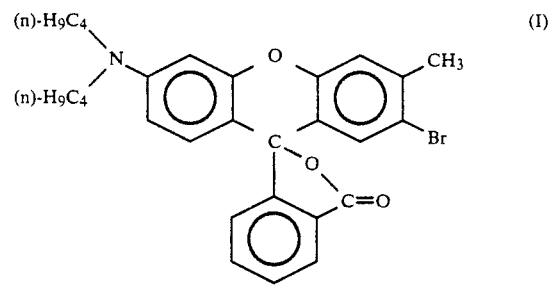

According to another aspect of the present invention, there is provided a pressure-sensitive record material comprising a support sheet and a chromogenic layer applied onto the support sheet. The chromogenic layer contains therein the fluoran compound represented by the formula (I) in the form of microcapsules or dispersion.

When the preseure-sensitive record material is put upon a developer sheet onto which a developer is applied and a pressure is applied on the record material, a clear vermilion color is developed on the developer sheet.

DETAILED DESCRIPTION OF THE INVENTION

The fluoran compound of the present invention is a colorless or slightly colored solid substance and is stable in air. It develops a vermilion color immediately after it contacts an acidic substance. The color-developed substance has an excellent light resistance, solubility in a pressure-sensitive oil and sublimation resistance, so that it is of great utility value.

The following table shows a comparison in the sublimation resistance between the above-described known fluoran compound A and the fluoran compound of the present invention, i.e. 2-bromo-3-methyl-6-N, N-di-n- butylaminofluoran (hereinafter referred to as compound I):

| Compound | Color density* |
| --- | --- |
| Known compound (A) | 0.19 |
| Compound (I) of this invention | 0.09 |

*A higher color density means a lower sublimation resistance.

Testing method of color density

A 2% solution of the fluoran compound in toluene was prepared and 20 μl of this solution was spotted on a filter paper and dried. This filter paper was sandwiched between developer paper sheets cantaining clay as a developer, further sandwiched between glass plates and then applied a load of 5 g/cm² at 100° C. for 1 hour. After the application of the load, the density of color developed on the developer paper sheets was measured by using a Macbeth reflective density meter (filter: Wratten #106).

As being understood from the above table, the fluoran compound (I) of the present invention is excellent in sublimation resistance, and therefore, when it is used as a chromogenic substance of a pressure-sensitive record material, an excellent record material without causing any stain due to re-sublimation can be obtained.

The fluoran compound (I) of the present invention can be prepared by the following process.

An benzene derivative represented by the general formula [II]

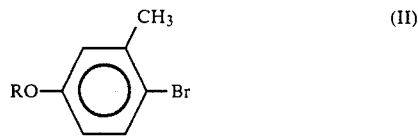

(wherein R is a hydrogen atom, an alkyl group having 1 to 4 carbon atoms or an acetyl group) is reacted with a benzophenone compound represented by the formula [III]

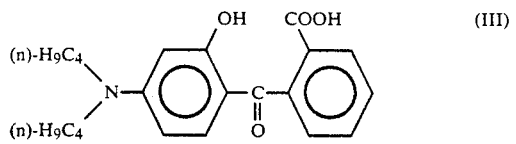

for several hours at a temperature of 0 to 80° C. in the presence of a condensing agent, e.g. concentrated sulfuric acid. After the reaction, the reaction mixture is poured into water, and the pH is adjusted to 8 to 10 by the addition of sodium hydroxide to produce precipitate. To a cake obtained by filteration of the precipitate are added toluene and a 5 to 10% aqueous solution of sodium hydroxide. The resulting mixture is agitated under reflux for 1 to 3 hours, and the toluene phase is separated, recovered, washed with water, and concentrated. The crystals are precipitated and recovered by filtration and then dried to obtain slightly colored fluoran compound (I) of the present invention in high purity and high yield. If necessary, it may be recrystallized from a volatile organic solvent such as toluene, acetone, butyl acetate or hexane.

Examples of condensing agents employed in the process for preparing the fluoran compound (I) include acetic anhydride, phosphoric acid, polyphosphoric acid, phosphorus oxychloride, zinc chloride and the like, as well as the above-described concentrated sulfuric acid. Among these condensing agents, concentrated sulfuric acid is preferable, since it serves not only as a condensing agent but also as a solvent for the benzophenone compound represented by the formula (III).

The pressure-sensitive record material such as, for example, a pressure-sensitive copying paper according to the present invention can be produced by the following process.

The chromogenic substance of the fluoran compound (I) or a mixture thereof with other chromogenic substances is dissolved in a solvent such as a synthetic oil (diarylalkane, e.g. an alkylated naphthalene, an alkylated diphenyl, an alkylated diphenylmethane or the like; an alkylated terphenyl or the like), a vegitable oil (cotton oil, castor oil or the like), an animal oil, a mineral oil, or a mixture thereof. The resulting solution is then dispersed in a binder or encapsulated in microcapsules. The dispersion or microcapsules thus produced is applied onto a support sheet such as paper, plastic sheet, resin-coated paper or the like.

The amount of the chromogenic substance used in the production of the record material is determined according to the desired applying thickness on the support sheet, the form of the pressure-sensitive copying paper, the process by which the microcapsules are prepared, and other factors. The encapsulation of the chromogenic substance may be preferably carried out by the process utilizing the coacervation of a hydrophilic colloid sol disclosed in U.S. Pat. Nos. 2,800,457 and 2,800,458, or by the process of the interfacial polymerization disclosed in British Pat. Nos. 867,797 and 1,091,076.

Typical developers which can be used together with the pressure-sensitive record material of the present invention include clays (acid clay, activated clay, attapulgite, kaolin or the like), phenolic resins, and polyvalent metal salts of aromatic carboxylic acids. More particularly, the phenolic resins include a phenol-aldehyde polymer (the so-called novolac type) and a phenol-acetylene polymer. The polyvalent metal salts of aromatic carboxylic acids are those described in, for example, U.S. Pat. Nos. 3,864,146, 3,983,292, 3,934,070 and 3,983,292.

As the aromatic carboxylic acid in the above-described polyvalent metal salts of aromatic carboxylic acids, those having a hydroxyl group in the ortho- or para-position with respect to the carboxyl group are useful. Among them, salicylic acid derivatives are preferable, and those having a substituent such as an alkyl group, an aryl group or an aralkyl group in one or both of ortho- and para-positions with respect to the hydroxyl group and having at least eight carbon atoms in total in all of the substituents are especially preferable.

The present invention will now be described hereinbelow with reference to the following examples. It should not be construed that the present invention is limited only to these examples.

EXAMPLE 1

22.1 g of 2-hydroxy-4-N,N-di-n-butylamino-2'-carboxybenzophenone was added to 150 g of 98 % sulfuric acid and dissolved completely at about 20° C. 10.0 g of 2-methyl-4-methoxybromobenzene was added to this solution to conduct a reaction for 5 hours at a temperature of about 10° to 20° C. After the reaction, the reaction mixture was poured into 1 l of ice-water and a 10 % aqueous solution of sodium hydroxide was then added to the reaction mixture to adjust the pH to 7 to 8 and to produce precipitate. The resulting precipitate was recovered by filtration and 300 ml of toluene and 150 ml of a 10% aqueous solution of sodium hydroxide were added to the obtained cake and agitated under reflux for 2 hours. The toluene phase was separated, washed with water, concentrated to dryness, and solidified by the addition of methanol. The solidified product was dried to yield 19.1 g of light-pink 2-bromo-3-methyl-6-N,N-di-n-butylaminofluoran (compound (I)). Its melting point was 176.4° to 177.6° C. Its $\lambda_{max}$ and a molecular extinction coefficient measured in 95% acetic acid were 393 nm ($1.15 \times 10^4$), 502 nm ($3.22 \times 10^4$) and 535 nm ($2.77 \times 10^4$). A solution prepared by dissolving this compound in toluene was colorless and quickly developed a vermilion color when it contacts silica gel.

EXAMPLE 2

1.35 g of the fluoran compound (I) of this invention, i.e., 2-bromo-3-methyl-6-N,N-di-n-butylaminofluoran was dissolved in 43.65 g of an alkylnaphthalene. 67.5 g of an emulsifying agent (5% SCRIPSET #520, a product of Monsanto Co.) was added to this solution to prepare an emulsion with a homomixer.

Separately, 5.6 g of melamine, 17 g of a 37% aqueous solution of formalin and 37.4 g of water were mixed together. After the pH of the resulting mixture was adjusted to about 9, methylolmelamine was prepared therefrom at 60° C. To this reaction solution was added the above-mentioned emulsion dropwise to prepare a methylene compound at 80° C. and produce a dispersion of microcapsules. 68 g of a 10% aqueous solution of PVA was added as a binder to the dispersion of microcapsules and the resulting dispersion was applied onto paper and dried. The thus obtained pressure-sensitive copying paper had an excellent storage stability.

In order to evaluate the performance of this pressure-sensitive copying paper, it was put upon various kind of developer paper, i.e. clay paper, resin paper and organic acid salt paper, and a pressure equivalent to a writing pressure was applied on the pressure-sensitive copying paper.

The various kind of developer paper were prepared in the following manner (parts are by weight):

Clay paper 20 parts of acid clay, 0.2 part of sodium hexameta phosphate and 80 parts of water were dispersed together for 5 minutes with a homogenizer, and 5 parts of a 50% styrenebutadiene latex was added to obtain a clay dispersion. This dispersion was applied to wood free paper in an amount of 5 g/m² by dry solid matter weight to obtain clay paper.

Resin paper 20 parts of a p-phenylphenol-formalin condensate, 100 parts of calcium carbonate and 600 parts of a 2% aqueous solution of polyvinyl alcohol were dispersed together with a ball mill to obtain a phenolic resin dispersion. This dispersion was applied to wood free paper in an amount of 5 g/m² by dry solid matter weight to obtain resin paper.

Organic acid salt paper

This paper was prepared in the same manner as that of the preparation of the resin paper except that the p-phenylphenol-formalin condnsate was replaced by zinc 3,5-di-α-methylbenzylsalicylate.

When the copying paper prepared by using the fluoran compound (I) of this invention as a chromogenic substance was put on each developer paper and a pressure was applied to each, an image having a vermilion color could be instantaneously formed on each developer paper. These images were high in fresh color density and excellent in light fastness and sublimation resistance.

The results of evaluation are shown in the following table. 2-Chloro-3-methyl-6-diethylaminofluoran (compound A) was listed as a contorl example.

| | Developer paper | | | | | | | | |
|---|---|---|---|---|---|---|---|---|---|
| | Clay paper | | | Resin paper | | | Organic acid salt paper | | |
| | Df *1 | R % *2 | Ds *3 | Df | R % | Ds | Df | R % | Ds |
| Compound of this invention | 0.53 | 74 | 0.06 | 0.52 | 85 | 0.06 | 0.50 | 92 | 0.06 |
| Compound (A) as control | 0.54 | 72 | 0.08 | 0.53 | 83 | 0.09 | 0.51 | 94 | 0.11 |

Notes
*1 Df: fresh color density: a value obtained when a copying paper was put on a developing paper, a pressure of 500 kg/cm² was applied to an area of 28 mm φ with a hydraulic press to allow this area to develop a color, and the color-developed image was measured for its color density with a Macbeth reflection densitometer (filter: Wratten # 106).
*2 R %: light fastness value: a value obtained when the color-develpoed image obtained in the above-mentioned item (*1) was exposed to light for 1 hour with a Fade-Ometer, the density of the color-developed image after exposure was measured, and calculation was made according to the following equation:

light fastness value = $\dfrac{\text{density after 1-hour exposure}}{\text{fresh color density}} \times 100$ (%).

*3 Ds: sublimation resistance: a value obtained when the color-developed image obtained in the above-mentioned item (*1) was sandwiched between developer paper sheets and further sandwiched between glass plates, the product was tested for 1 hour at 100° C. under an applied load of 5 g/cm², and the color densities of the developer papers were measured.

As is understood from the foregoing, by using the novel fluoran compound (I), i.e. 2-bromo-3-methyl-6-N,N- di-n-butylaminofluoran according to the pre-sent invention as a chromogenic substance, there is provided a pressure-sensitive recorde material which can develop an image of a clear vermilion color having a high color density, excellent light fastness and excellent sublimation resistance.

What is claimed is:
1. A fluoran compound repre-sented by the formula (I):

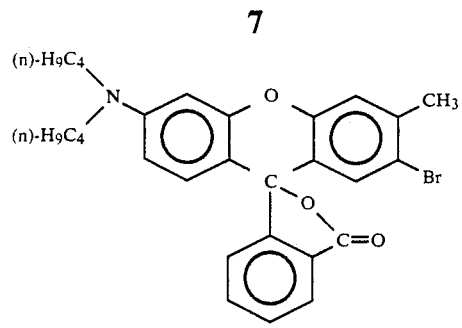 (I)
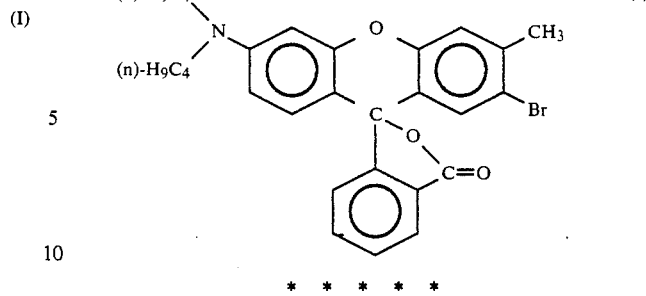 (I)